US00PP17002P2

(12) United States Plant Patent
Eggleton

(10) Patent No.: US PP17,002 P2
(45) Date of Patent: Aug. 15, 2006

(54) ***GAURA* PLANT NAMED 'PASSIONATE RAINBOW'**

(50) Latin Name: *Gaura lindheimeri*
Varietal Denomination: Passionate Rainbow

(76) Inventor: Steven Eggleton, 3 Harris Road, Wonga Park, Melbourne, Vic (AU), 3115

( * ) Notice: Subject to any disclaimer, the term of this patent is extended or adjusted under 35 U.S.C. 154(b) by 185 days.

(21) Appl. No.: 10/805,621

(22) Filed: Mar. 22, 2004

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell

(57) ABSTRACT

A new cultivar of *Gaura* plant named 'Passionate Rainbow' characterized by dense growth habit, red-pink and cream-white variegation, and red-pink flowers. In combination these traits set 'Passionate Rainbow' apart from all other existing varieties of *Gaura* known to the inventor.

2 Drawing Sheets

Genus: *Gaura.*
Species: *lindheimeri.*
Denomination: Passionate Rainbow.

BACKGROUND OF THE INVENTION

The present invention relates to a new and distinct variety of butterfly bush grown for use as an ornamental plant for use in the landscape. The new cultivar is known botanically as *Gaura lindheimeri* and will be referred to hereinafter by the cultivar name 'Passionate Rainbow'.

'Passionate Rainbow' was first observed by the inventor in November 2001 as an individual naturally occurring variegated whole plant sport growing amongst a crop of plants of the non-variegated variety *Gaura lindheimeri* 'Passionate Pink' (unpatented) in a cultivated area of Victoria, Australia.

By January 2002, the inventor was able to take and root ten stem cuttings from the observed sport, 'Passionate Rainbow'. The resulting plants exhibited the same characteristics of variegated foliage as the originally discovered sport. Since then, the inventor has asexually propagated many further generations, and has determined that the characteristics of 'Passionate Rainbow' have remained stable and that 'Passionate Rainbow' reproduces true to type during successive generations of asexual reproduction.

When compared with the presumed parental cultivar, *Gaura lindheimeri* 'Passionate Pink', the leaves of 'Passionate Rainbow' exhibit variegation, while the leaves of *Gaura lindheimeri* 'Passionate Pink' are entirely absent of variegation. 'Passionate Rainbow' exhibits a dense upright growth habit, variegated foliage, and red-pink flowers.

The closest comparison plants to 'Passionate Rainbow' known to the inventor are the variegated varieties *Gaura lindheimeri* 'Sunny Butterflies' (unpatented) and *Gaura lindheimeri* 'Bijou Butterflies' (U.S. Plant Pat. No. 15,479). 'Passionate Rainbow' is distinguishable from *Gaura lindheimeri* 'Sunny Butterflies' by the color of variegation. The variegated foliage of 'Passionate Rainbow' is prominently tinged with red-pink towards the apex, whereas the foliage of 'Sunny Butterflies' foliage is uniformly yellow and cream-white.

'Passionate Rainbow' is distinguishable from *Gaura lindheimeri* 'Bijou Butterflies' by density of plant habit. 'Passionate Rainbow' exhibits a dense form, while *Gaura lindheimeri* 'Bijou Butterflies' exhibits greater density.

SUMMARY OF THE INVENTION

The following traits have been repeatedly observed and represent the distinguishing characteristics of the new plant cultivar 'Passionate Rainbow'. In combination these traits set 'Passionate Rainbow' apart from all other *Gaura* known to the inventor. 'Passionate Rainbow' has not been tested under all possible conditions and phenotypic differences may be observed with variations in environmental, climatic and cultural conditions, however, without any variance in genotype.

1. *Gaura* 'Passionate Rainbow' exhibits a dense, upright habit.
2. *Gaura* 'Passionate Rainbow' exhibits red-pink flowers.
3. The foliage of *Gaura* 'Passionate Rainbow' exhibits cream-white variegation with red-pink coloration towards the apex.
4. *Gaura* 'Passionate Rainbow' is propagated using vegetative stem cuttings.
5. *Gaura* 'Passionate Rainbow' is hardy in USDA Zones 5–10.
6. In one growing season, *Gaura* 'Passionate Rainbow' reaches approximately 25 cm in height and 20 cm–25 cm in width in a 1-liter container.

BRIEF DESCRIPTION OF THE DRAWINGS

The accompanying color drawings illustrate the overall appearance of the new *Gaura* cultivar 'Passionate Rainbow' showing the colors as true as it is reasonably possible to obtain in colored reproductions of this type. Colors in the drawings may differ from the color values cited in the detailed botanical description, which accurately describe the actual colors of the new variety 'Passionate Rainbow'.

The drawing labeled as FIG. 1 illustrates a six months old plant of 'Passionate Rainbow' in first flower.

Figure 1:
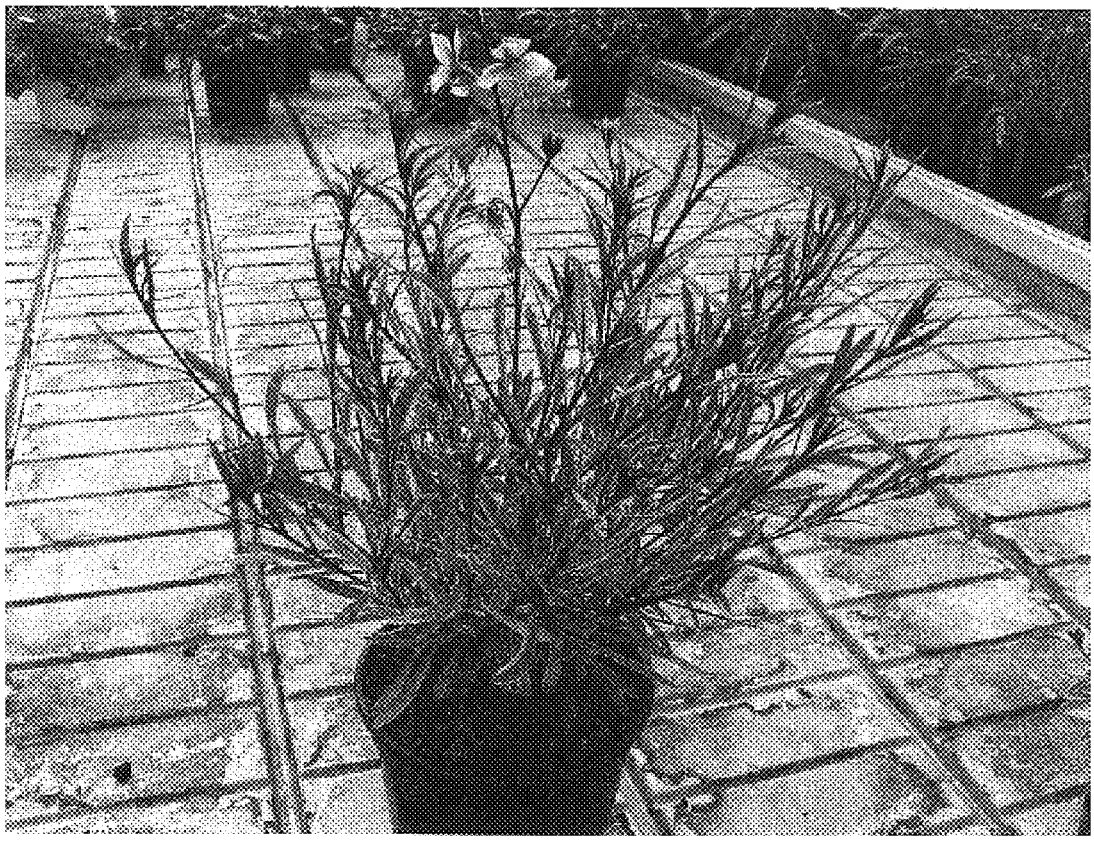
Figure 2:
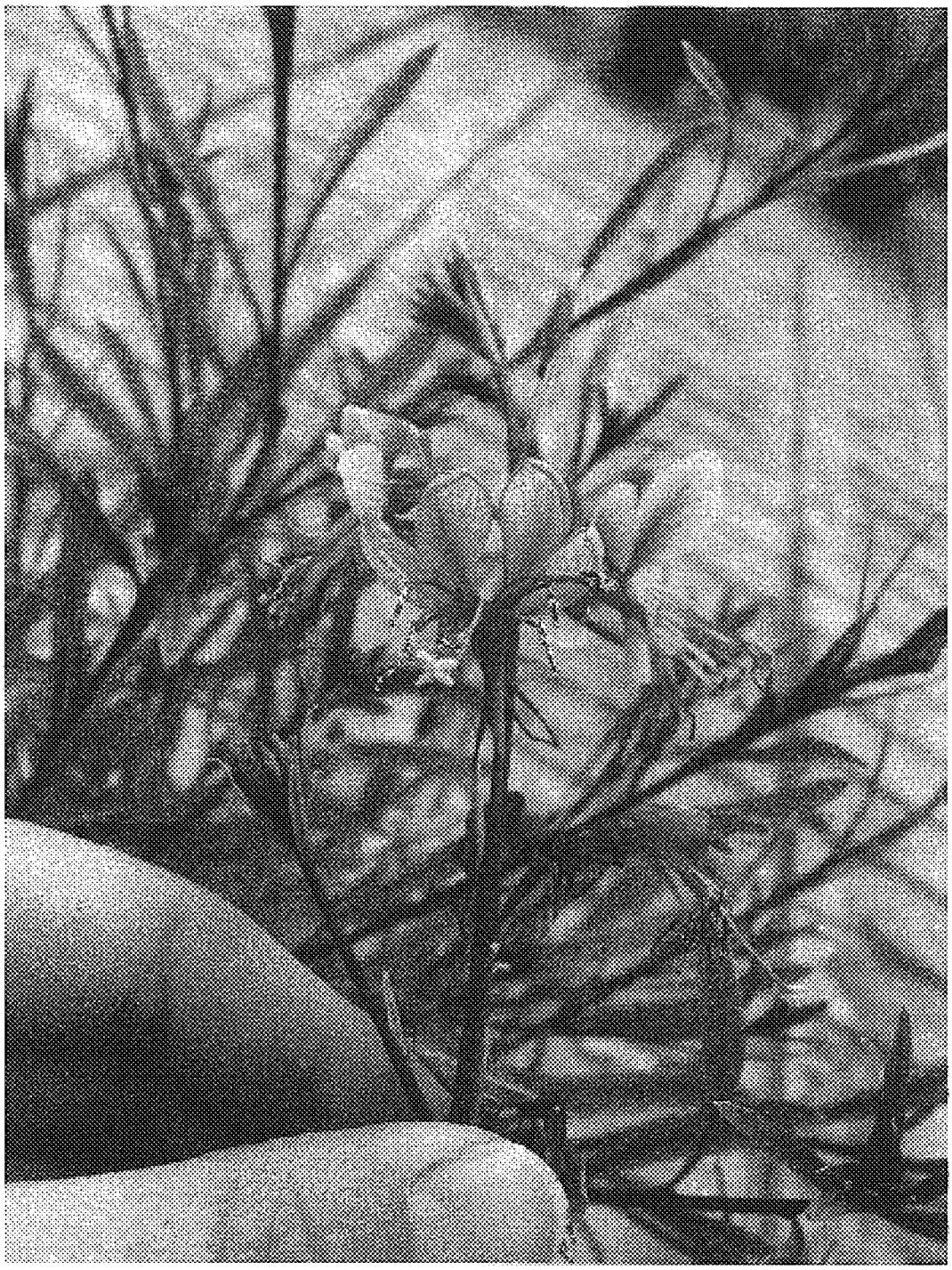

The drawing labeled as FIG. 2 illustrates the flower of 'Passionate Rainbow'.

Both drawings were made from digital images of plants grown in an unheated greenhouse in Naaldwijk, The Netherlands. Colors in the drawings may appear different from actual colors due to light reflectance.

BOTANICAL DESCRIPTION OF THE PLANT

The following is a detailed description of the new *Gaura* plant named 'Passionate Rainbow'. Data was collected in Arroyo Grande, Calif. from 6-month-old plants that were grown in 1-liter containers out-of-doors in full sun. The color determinations are in accordance with the 2001 Royal Horticultural Society Colour Chart of The Royal Horticultural Society, London, England, except where general color terms of ordinary dictionary significance are used. The growing requirements are similar to other *Gaura*.

Botanical classification: *Gaura* 'Passionate Rainbow'.
Species: *lindheimeri*.
Commercial classification: Perennial.
Common name: Butterfly bush.
Use: Ornamental plant for use in the landscape.
Cultural requirements: Plant in well-drained moderately fertile soil in full sun.
Pests and disease: No susceptibility or resistance to pests or disease are known to the inventor.
Root system: Deep rooting makes the plant very drought tolerant.
Parentage: 'Passionate Rainbow' arose as a naturally occurring sport of *Gaura* 'Passionate Pink'.
Plant description:
- *Bloom period.*—Late spring to fall.
- *Growth habit.*—Dense, upright growth habit.
- *Plant height.*—25 cm. in height at 6 months in a 1-liter container.
- *Plant width.*—20 cm–25 cm. in width at 6 months in a 1-liter container.
- *Plant hardiness.*—USDA Zones 5–10.
- *Propagation.*—Propagation is accomplished using vegetative stem cuttings.
- *Time to develop roots.*—2–3 weeks are needed for initial cuttings to develop roots.
- *Crop time.*—6 months are needed to produce a finished 1-liter container from a rooted cutting.

Stem:
- *Stem shape.*—Cylindrical.
- *Stem color.*—Colors 147B and 183A are individually present on stem.
- *Stem texture.*—Flexible.
- *Stem width.*—2 mm. in width.
- *Stem length.*—16–19 cm. in length.
- *Stem surface.*—Glabrous.
- *Internode length.*—Average internode length is 1 cm.

Foliage:
- *Shape.*—Oblanceolate.
- *Division.*—Simple.
- *Apex.*—Acuminate.
- *Base.*—Attenuate.
- *Venation pattern.*—Pinnate.
- *Vein color* (*adaxial surfaces*).—187A.
- *Vein color* (*abaxial surfaces*).—187A.
- *Margins.*—Entire.
- *Attachment.*—Sessile.
- *Arrangement.*—Alternate and spiraling.
- *Leaf surface* (*adaxial surface*).—Glabrous.
- *Leaf surface* (*abaxial surface*).—Glabrous.
- *Leaf appearance.*—Matte.
- *Leaf length.*—Leaf length ranges from 1.5 cm. to 4 cm. in length.
- *Leaf width.*—Leaf width ranges from 0.25 cm. to 0.50 cm. in width.
- *Leaf color* (*adaxial surfaces*).—147A and 158B are both present on an individual leaf. Newly emerging and emerged leaves suffused with 58A.
- *Leaf color* (*abaxial surfaces*).—147A and 158B are both present on an individual leaf. Newly emerging and emerged leaves suffused with 58A.
- *Fragrance.*—None observed.

Flowers:
- *Inflorescence.*—Panicle.
- *Shape.*—Stellate.
- *Sexuality.*—Bisexual.
- *Flower dimensions.*—Depth 2 cm; diameter 3 cm.
- *Flower color.*—A combination of colors N57B and N57C are present.
- *Flowers persistent or self-cleaning.*—Self-cleaning.
- *Aspect.*—Facing outward.
- *Bud dimensions.*—2 mm. in width and 8 mm. in length.
- *Number of buds.*—20–25 buds per panicle.
- *Bud shape.*—Linear.
- *Bud color.*—59A.
- *Bud surface.*—Puberulent.
- *Number of buds per peduncle.*—An average of 10–15 buds per peduncle.
- *Bud apex.*—Acute.
- *Petals.*—Four in number.
- *Petal opening and shape.*—Petals open claw shaped and flatten to explanate.
- *Petal color* (*adaxial surface*).—Colors N57B and N57C are individually present on an individual flower.
- *Petal color* (*abaxial surface*).—Colors N57B and N57C are individually present on an individual flower.
- *Petal shape.*—Closest to ovate.
- *Petal length.*—15 mm.
- *Petal width.*—1 cm. in width.
- *Petals fused or unfused.*—Unfused.
- *Petal margin.*—Entire.
- *Petal apex.*—Acute.
- *Petal base.*—Cuneate.
- *Petal surface.*—Glabrous.
- *Sepals.*—Four (spur-like).
- *Sepal dimensions.*—1.50 cm. in length and 2 mm. in width.
- *Sepal color.*—58A.
- *Sepal apex.*—Acute.
- *Sepal base.*—Truncate.
- *Sepal margin.*—Entire.
- *Sepal surface.*—Glabrous.
- *Pedicel dimensions.*—6 mm. in length and 1.50 mm. in width.
- *Pedicel color.*—183A. Pedicel shape: Cylindrical.
- *Pedicel color.*—187B.
- *Pedicel surface.*—Glabrous.
- *Calyx.*—Absent.
- *Flower fragrance.*—Slight scent observed.
- *Lastingness of flower.*—24–48 hours on the plant; less than 24 hours off the plant.

Reproductive organs:

*Stamens.*—Eight in number.

*Stamen color.*—59D.

*Stamen dimensions.*—8 mm. in length and 0.50 mm. in diameter.

*Anther color.*—59A.

*Anther dimensions.*—3 mm. in length and 0.20 mm. in width.

*Quantity of pollen.*—Small amount.

*Color of pollen.*—59A.

*Pistil.*—One in number.

*Pistil dimensions.*—1.50 cm. in length and 0.50 mm. in width.

*Pistil color.*—61A.

*Pistil shape.*—Filament.

*Style color.*—61A.

*Stigma shape.*—Four lobed.

*Stigma color.*—61A.

*Stigma dimensions.*—2 mm. in height and 2 mm. in width.

*Ovary position.*—Inferior.

*Ovary color.*—139A.

*Ovary shape.*—Ovate.

*Ovary dimensions.*—3 mm. in length and 3 mm. in diameter.

Seed production: No seed observed to date.

What is claimed is:

1. A new and distinct cultivar of *Gaura* plant named 'Passionate Rainbow' as described and illustrated herein.

* * * * *